(12) United States Patent
Watanabe

(10) Patent No.: US 7,361,449 B2
(45) Date of Patent: Apr. 22, 2008

(54) SPECIFIC DYE COMPOUND, OPTICAL INFORMATION RECORDING MEDIUM COMPRISING SPECIFIC DYE, AND INFORMATION RECORDING METHOD USING THIS OPTICAL INFORMATION RECORDING MEDIUM

(75) Inventor: Tetsuya Watanabe, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 548 days.

(21) Appl. No.: 10/853,204

(22) Filed: May 26, 2004

(65) Prior Publication Data

US 2004/0259031 A1     Dec. 23, 2004

(30) Foreign Application Priority Data

Jun. 17, 2003   (JP)   ............................. 2003-171795

(51) Int. Cl.
G11B 7/24      (2006.01)
C07D 249/16    (2006.01)

(52) U.S. Cl. ................ 430/270.15; 430/945; 428/64.8; 548/257

(58) Field of Classification Search ................ 548/257; 430/512
See application file for complete search history.

(56) References Cited

U.S. PATENT DOCUMENTS

| | | | | |
|---|---|---|---|---|
| 4,396,712 A | * | 8/1983 | Kinoshita et al. | 430/614 |
| 4,412,231 A | * | 10/1983 | Namba et al. | 346/135.1 |
| 4,727,158 A | * | 2/1988 | Seltzer et al. | 548/260 |
| 4,826,888 A | * | 5/1989 | Sasaki et al. | 522/26 |
| 4,871,644 A | * | 10/1989 | Bauer | 430/191 |
| 5,278,314 A | * | 1/1994 | Winter et al. | 548/259 |
| 5,280,124 A | * | 1/1994 | Winter et al. | 548/259 |
| 5,319,090 A | * | 6/1994 | MacLeay et al. | 548/257 |
| 5,332,608 A | * | 7/1994 | Tsuji et al. | 428/64.8 |
| 5,679,494 A | * | 10/1997 | Minami et al. | 430/138 |
| 5,808,086 A | * | 9/1998 | Sugii et al. | 548/260 |
| 5,922,882 A | * | 7/1999 | Mori et al. | 548/260 |
| 5,985,444 A | * | 11/1999 | Olson et al. | 428/357 |
| 6,166,218 A | * | 12/2000 | Ravichandran et al. | 548/257 |
| 6,855,389 B2 | * | 2/2005 | Konishi et al. | 428/64.1 |
| 2001/0037037 A1 | * | 11/2001 | Dietliker et al. | 562/30 |
| 2002/0035175 A1 | * | 3/2002 | Wood et al. | 524/91 |
| 2002/0061381 A1 | * | 5/2002 | Saito | 428/64.4 |
| 2002/0171606 A1 | * | 11/2002 | Yabuki | 345/37 |
| 2003/0103442 A1 | * | 6/2003 | Kakuta et al. | 369/275.4 |
| 2003/0118938 A1 | * | 6/2003 | Ishida et al. | 430/270.16 |
| 2003/0148215 A1 | * | 8/2003 | Kakuta et al. | 430/270.15 |
| 2004/0029056 A1 | * | 2/2004 | Tsukada | 430/611 |
| 2004/0192927 A1 | * | 9/2004 | Pastor et al. | 548/257 |
| 2004/0259031 A1 | * | 12/2004 | Watanabe | 430/270.15 |

FOREIGN PATENT DOCUMENTS

| | | | |
|---|---|---|---|
| JP | 05-078517 | * | 3/1993 |
| JP | 10-278434 | * | 10/1998 |
| JP | 2000-178276 | * | 6/2000 |
| JP | 2001-160240 A | | 6/2001 |
| JP | EP 1 193 699 | * | 4/2002 |
| JP | 2002-172865 A | | 6/2002 |

* cited by examiner

Primary Examiner—Mark F. Huff
Assistant Examiner—Anna L. Verderame
(74) Attorney, Agent, or Firm—Sughrue Mion, PLLC

(57) ABSTRACT

The present invention provides an optical information recording medium comprising a substrate having disposed thereon a recording layer, wherein the recording layer includes a recording dye represented by the following formula (I) or (II):

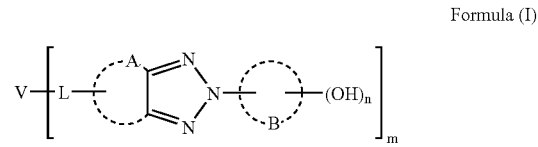

Formula (I)

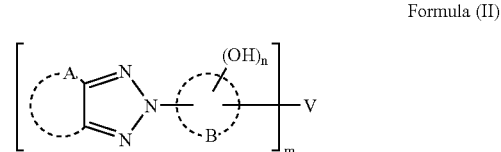

Formula (II)

wherein A represents an aromatic ring which may have a substituent, B represents an aromatic ring which may have a substituent other than a hydroxyl group, n is an integer of 1 to 3, m is an integer of 2 to 6, L represents a bivalent linking group, which may have a substituent, or a single bond, and V represents an aromatic ring, which may have a substituent other than L.

13 Claims, No Drawings

SPECIFIC DYE COMPOUND, OPTICAL INFORMATION RECORDING MEDIUM COMPRISING SPECIFIC DYE, AND INFORMATION RECORDING METHOD USING THIS OPTICAL INFORMATION RECORDING MEDIUM

CROSS-REFERENCE TO RELATED APPLICATION

This application claims priority under 35 USC 119 from Japanese Patent Application No. 2003-171795, the disclosure of which is incorporated by reference herein.

BACKGROUND OF THE INVENTION

1. Field of the Invention

The present invention relates to an optical information recording medium, to an information recording method capable of recording and reproducing information by using a laser, and to a dye compound. In particular, the invention relates to a heat mode type optical information recording medium, to an information recording method suitable for recording information by using a short wavelength laser having a wavelength of 440 nm or less, and to a dye compound.

2. Description of the Related Art

An optical information recording medium (optical disc) capable of recording information only once by using a laser has been conventionally known. This disc is called a write-once type CD (the so-called CD-R). The disc typically has a structure in which a recording layer made of an organic dye, a light-reflective layer made of a metal such as gold and a protective layer made of a resin are laminated on a transparent disc substrate in that order. Information is recorded on the CD-R by radiating onto the CD-R near infrared ray laser beams, which usually have a wavelength of around 780 nm. Specifically, the laser-radiated portions of the recording layer absorb the light, so that the temperature of the portions rises locally. Consequently, the physical or chemical properties of the portions change (for example, generation of pits), and information is recorded as a result of the optical properties of the portions being changed.

Meanwhile, the information is read (reproduced) by radiating onto the recording layer laser beams having the same wavelength as those of the recording laser beams. Specifically, information is reproduced by detecting the difference between reflectivity of portions of the recording layer having a changed optical property (recorded portions) and reflectivity of portions of the recording layer having an unchanged optical property (non-recorded portions).

In recent years, optical information recording media having a higher recording density have been demanded. To meet such a demand, an optical disc called a recordable digital versatile disc (the so-called DVD-R) has appeared on the market ("Nikkei New Media", special edition "DVD", published in 1995). This DVD-R has a structure in which two discs each having a recording layer made of a dye, a light-reflective layer which is usually formed on the recording layer, and, if necessary, a protective layer on a transparent disc-shaped substrate having a guide groove (a pregroove) which is tracked with radiated laser beams and whose width (i.e., 0.74 to 0.8 μm) is half or less of the width of grooves in CD-Rs, are bonded to each other with an adhesive so that the recording layer is disposed inside the DVD-R. Alternatively, the DVD-R has a structure in which the disc and a protective substrate having the same shape as the disc are bonded to each other with an adhesive so that the recording layer is disposed inside. The recording and reproducing of information in this DVD-R are performed by radiating onto the DVD-R visible laser beams, which usually have a wavelength of 630 to 680 nm. In the DVD-R, recordings of higher density can be attained than in the CD-R.

Recently, networks such as the Internet, and high-vision TV have been expanding rapidly. Moreover, the days of broadcasting by high definition television (HDTV) are also drawing near. Thus, demands are rising for large-capacity recording media capable of recording image information inexpensively and simply. Although the DVD-R is to some degree securing a position as a large-capacity recording medium, it cannot be said that the DVD-R has a level of recording capacity adequate to satisfy future demands. Thus, developments are being made in optical discs for which laser beams having a wavelength shorter than the wavelength of laser beams used for the DVD-R can be employed, and which discs accordingly have an improved recording density and a superior recording capacity.

For example, various recording and reproducing methods have been disclosed wherein an optical information recording medium having a recording layer containing an organic dye is used to record and reproduce information by radiating onto the medium from the recording layer side toward the light-reflective layer side laser beams having a wavelength of 530 nm or less (see, for example, Japanese Patent Applications Laid-Open (JP-A) Nos. 4-74690, 8-127174, 11-53758, 11-334204, 11-334205, 11-334206, 11-334207, 2000-43423, 2000-108513, 2000-113504, 2000-149320, and 2000-158818). Specifically, an information recording and reproducing method has been proposed for recording and reproducing information by radiating blue laser beams (wavelength: 430 or 488 nm) or bluish green laser beams (wavelength: 515 nm) onto an optical disc having a recording layer made of a dye such as a porphyrin compound, an azo dye, a metal azo dye, a quinophthalone dye, a trimethine cyanine dye, a dicyanovinylphenyl skeleton dye, or a coumalin compound.

As a result of research conducted by the inventor of the invention, however, it has been become evident that the above-mentioned optical discs are deficient in terms of recording properties such as practical sensitivity, reflectivity and degree of modulation and that further improvements are accordingly required. The optical discs are also deficient in terms of heat and humidity stability and in terms of light stability. Furthermore, there are also problems concerning the strength, or the film quality, of the recording film of the optical discs, and improvements in these properties are also necessary.

For the purpose of these improvements, JP-A No. 2002-172865 discloses an optical information recording medium having a recording layer including a 1,2,3-triazole compound and, in order to record information into the medium, a method of radiating onto this medium laser beams having an oscillation wavelength of 405 nm. In this method, however, the performance of optical information recording media stipulated as preferable examples has not yet proved satisfactory.

Accordingly, dye compounds and optical information recording media are required which are capable of recording and reproducing information by using laser beams having a shorter wavelength than those of laser beams used for CD-Rs or DVD-Rs, particularly laser beams which have a wavelength of 440 nm or less, and which also have excellent recording properties.

Dye compounds and optical information recording media are also required which are superior in terms of heat and humidity stability and in terms of light stability, and which are also satisfactory in terms of the strength and quality of the resultant recording layers.

Further, an information recording method is required which is capable of recording information at a high density, using an optical information recording medium having a recording layer which contains a dye compound having a high sensitivity to short wavelength laser beams.

SUMMARY OF THE INVENTION

As a result of eager investigation, the inventor of the invention has devised an optical information recording medium and an information recording method which have superior recording and reproducing properties such as a high sensitivity to short wavelength laser beams having a wavelength of 440 nm or less, a high reflectivity and a high degree of modulation, by using a specific recording dye (dye compound) as a recording material in a recording layer.

The inventor has also devised an optical information recording medium which is superior in terms of heat and humidity stability and in terms of light stability and is also satisfactory in terms of the strength and film quality of the recording layer formed in the medium.

A first aspect of the invention provides an optical information recording medium comprising a substrate having disposed thereon a recording layer, wherein the recording layer includes a recording dye represented by either of the following formulae (I) and (II):

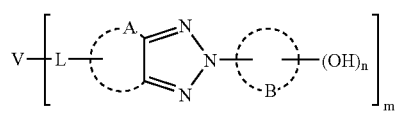

Formula (I)

wherein A represents an aromatic ring which may have a substituent, B represents an aromatic ring which may have a substituent other than a hydroxyl group, n is an integer of 1 to 3, m is an integer of 2 to 6, L represents either a bivalent linking group, which may have a substituent, or a single bond, and V represents an aromatic ring, which may have a substituent other than L,

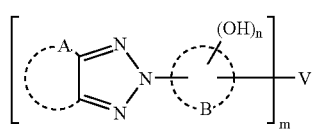

Formula (II)

wherein A, B, V, n and m represent the same definitions as those of A, B, V, n and m in formula (I), respectively.

A second aspect of the invention provides a dye compound represented by either of the following formulae (V) and (VI):

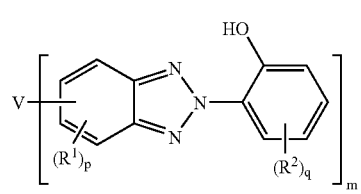

Formula (V)

wherein $R^1$ and $R^2$ each independently represent a substituent, p and q are each an integer of 0 to 3, m is an integer of 2 or 3, and V represents an aromatic ring, which may have a substituent,

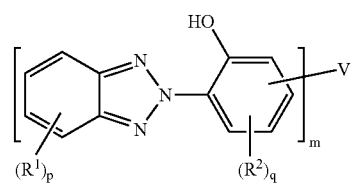

Formula (VI)

wherein $R^1$, $R^2$, p, q, V and m represent the same definitions as those of $R^1$, $R^2$, p, q, V and m in formula (V), respectively.

A third aspect of the invention provides a method of recording information onto an optical information recording medium comprising: providing an optical information recording medium comprising a substrate having disposed thereon a recording layer on which the information can be recorded by radiation of a laser, the recording layer comprising a recording dye represented by the above-illustrated formula (I) or (II), providing a laser that emits light having a wavelength of 440 nm or less, and using the laser to record information on the optical information recording medium. Examples of the optical information recording medium to which the information recording method of the invention can be applied include the above-mentioned optical information recording media and optical information recording media having embodiments described hereinafter.

The optical information recording medium and the dye compound of the invention enable recording and reproducing information with laser beams having a wavelength shorter than those of laser beams used for CD-Rs or DVD-Rs, particularly laser beams having a wavelength of 440 nm or less, and further have superior recording properties. They are also satisfactory in terms of heat and humidity stability and in terms of light stability. Moreover, a recording layer made of the dye is satisfactory in terms of strength and quality.

According to the information recording method of the invention, it is possible to record information at a high density by using the above-mentioned optical information recording medium, which has a recording layer that contains the dye compound having a high sensitivity to short wavelength laser beams.

DETAILED DESCRIPTION OF THE INVENTION

1. Optical Information Recording Medium

The optical information recording medium of the invention has a substrate and a recording layer including a recording dye represented by the following formula (I) or (II):

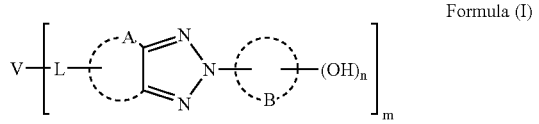

Formula (I)

wherein A represents an aromatic ring which may have a substituent, B represents an aromatic ring which may have a substituent other than a hydroxyl group, n is an integer of 1 to 3, m is an integer of 2 to 6, L represents a bivalent linking group, which may have a substituent, or a single bond, and V represents an aromatic ring, which may have a substituent other than L,

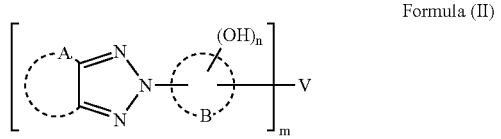

Formula (II)

wherein A, B, V, n and m represent the same definitions as those of A, B, V, n and m in formula (I), respectively.

Examples of the aromatic ring, which may have a substituent, represented by A or B in formula (I) or (II) include hydrocarbon aromatic rings such as benzene, naphthalene, anthracene and phenanthrene rings, and hetero aromatic rings such as pyridine, pyrimidine, quinoline, furan, pyrrole, and pyrazole rings. Preferable are benzene, naphthalene, and pyridine rings. Particularly preferable is a benzene ring.

Examples of the substituent of the aromatic ring represented by A or B in formula (I) or (II) include chain or cyclic substituted or unsubstituted alkyl groups having 1 to 20 carbon atoms (such as methyl, ethyl, isopropyl, cyclohexyl, benzyl, phenethyl, and trifluromethyl groups), substituted or unsubstituted aryl groups having 6 to 18 carbon atoms (such as phenyl, chlorophenyl, 2,4-di-t-amylphenyl, and 1-naphthyl groups), substituted or unsubstituted alkenyl groups having 2 to 20 carbon atoms (such as vinyl and 2-methylvinyl groups), substituted or unsubstituted alkynyl groups having 2 to 20 carbon atoms (such as ethynyl, 2-methylethynyl, and 2-phenylethynyl groups), halogen atoms (such as F, Cl, Br and I), a cyano group, a hydroxyl group, a carboxyl group, substituted or unsubstituted acyl groups having 2 to 20 carbon atoms (such as acetyl, benzoyl, salicyloyl, and pivaroyl groups), substituted or unsubstituted alkoxy groups having 1 to 20 carbon atoms (such as methoxy, butoxy, and cyclohexyloxy groups), substituted or unsubstituted aryloxy groups having 6 to 20 carbon atoms (such as phenoxy, 1-naphthoxy, and p-methoxyphenoxy groups), substituted or unsubstituted alkylthio groups having 1 to 20 carbon atoms (such as methylthio, butylthio, benzylthio, and 3-methoxypropylthio groups), substituted or unsubstituted arylthio groups having 6 to 20 carbon atoms (such as phenylthio, and 4-chlorophenylthio groups), substituted or unsubstituted alkylsulfonyl groups having 1 to 20 carbon atoms (such as methanesulfonyl, and butanesulfonyl groups), substituted or unsubstituted arylsulfonyl groups having 6 to 20 carbon atoms (such as benzenesulfonyl, and p-toluenesulfonyl groups), substituted or unsubstituted carbamoyl groups having 1 to 17 carbon atoms (such as unsubstituted carbamoyl, methylcarbamoyl, ethylcarbamoyl, n-butylcarbamoyl, and dimethylcarbamoyl groups), substituted or unsubstituted acylamino groups having 1 to 16 carbon atoms (such as acetylamino, and benzoylamino groups), substituted or unsubstituted acyloxy groups having 2 to 10 carbon atoms (such as acetoxy, and benzoyloxy groups), substituted or unsubstituted alkoxycarbonyl groups having 2 to 10 carbon atoms (such as methoxycarbonyl, and ethoxycarbonyl groups), 5- or 6-membered, substituted or unsubstituted heterocyclic groups (such as aromatic heterocyclic groups, for example, pyridyl, thienyl, furyl, thiazoyl, imidazoyl, and pyrazoyl groups, and non-aromatic heterocyclic groups, for example, pyrrolidine, piperidine, morpholine, pyran, thiopyran, dioxane, and dithiolane rings).

Preferable examples of the substituent of A or B in formula (I) or (II) are chain or cyclic substituted or unsubstituted alkyl groups having 1 to 16 carbon atoms, aryl groups having 6 to 14 carbon atoms, alkoxy groups having 1 to 16 carbon atoms, aryloxy groups having 6 to 14 carbon atoms, halogen atoms, a cyano group, alkoxycarbonyl groups having 2 to 17 carbon atoms, carbamoyl groups having 1 to 10 carbon atoms, and acylamino groups having 1 to 10 carbon atoms.

Among these groups, more preferable examples are chain or cyclic alkyl groups having 1 to 10 carbon atoms, aryl groups having 6 to 10 carbon atoms, alkoxy groups having 1 to 10 carbon atoms, aryloxy groups having 6 to 10 carbon atoms, a chlorine atom, a cyano group, alkoxycarbonyl groups having 2 to 11 carbon atoms, carbamoyl groups having 1 to 7 carbon atoms, and acylamino groups having 1 to 8 carbon atoms. Among these groups, particularly preferable examples are chain-branched or cyclic unsubstituted alkyl groups having 1 to 8 carbon atoms, unsubstituted alkoxy groups having 1 to 8 carbon atoms, unsubstituted alkoxycarbonyl groups having 3 to 9 carbon atoms, a cyano group, a phenyl group, and a chlorine atom.

In formal (I) or (II), the substituent of the aromatic ring represented by A or B may further have a substituent. Examples of the substituent in this case may be the same as those described as examples of the substituent of the aromatic ring represented by A or B.

In formulae (I) and (II), n is an integer of 1 to 3, preferably 1 or 2, and more preferably 1.

In formulae (I) and (II), m is an integer of 2 to 6, preferably 2 to 4, and more preferably 2 or 3. In formulae (I) and (II), partial structures divided by parentheses [ ], the number of which is m, may be the same or different.

In formula (I), L represents a bivalent linking group, which may have a substituent, or a single bond. Examples of L include —CONR$^3$—, —COO—, —O—, —S—, —SO—, —SO$_2$—, alkylene groups which may have a substituent, aryl groups which may have a substituent, and a single bond. Examples of the substituent which L may have are the same as those described as examples of the substituent of the aromatic ring represented by A or B in formula (I) or (II), and may be the partial structures included in the parentheses [ ] in formula (I) or (II). In this case, formula (I) or (II) can be a dendrimer.

L is preferably —CONR$^3$—, —COO— or a single bond, and more preferably —CONR$^3$— or a single bond. R$^3$ represents a hydrogen atom or a substituent. R$^3$ other than a hydrogen atom is preferably an alkyl group which may have a substituent, or an aryl group which may have a substituent. Bonding of V and L may take place in any direction.

In formulae (I) and (II), V represents an aromatic ring which may have a substituent other than L. Examples of V include substituted or unsubstituted aryl groups having 6 to 24 carbon atoms, and 5- or 6-membered substituted or unsubstituted heterocyclic groups.

In formulae (I) and (II), preferable examples of V are substituted or unsubstituted aryl groups having 6 to 18 carbon atoms, and 5- or 6-membered substituted or unsubstituted heterocyclic groups. More preferable examples thereof are substituted or unsubstituted aryl groups having 6 to 18 carbon atoms.

The compound represented by formula (I) or (II) is preferably a compound represented by the following formula (III) or (IV):

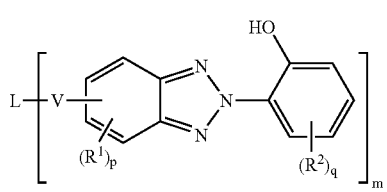

Formula (III)

wherein $R^1$ and $R^2$ each independently represent a substituent, p and q are each an integer of 0 to 3, m is an integer of 2 to 6, L represents a linking group, which has a valence of not less than bivalence, or a single bond, and V represents an aromatic ring, which may have a substituent other than L,

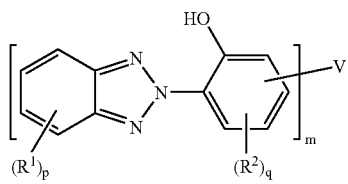

Formula (IV)

wherein $R^1$, $R^2$, p, q, V and m represent the same definitions as those of $R^1$, $R^2$, p, q, V and m in formula (III), respectively.

Examples and preferable examples of $R^1$ and $R^2$ in formulae (III) and (IV) are the same as those described as examples and preferable examples of the substituent of the aromatic ring represented by A or B in formula (I) or (II).

Examples and preferable examples of L and V in formulae (III) and (IV) are the same as those described as examples and preferable examples of L and V in formulae (I) and (II).

In formulae (III) and (IV), m is preferably an integer of 2 to 4, and more preferably 2 or 3.

Each of the recording dyes represented by formulae (I) and (II), and formulae (III) and (IV), which are included as subordinate formulae in formulae (I) and (II), preferably has at least one of the following characteristics 1 to 4 in light of the dye being applied to the recording layer of an optical information recording medium:

1. The dye is preferably dissolved in an organic solvent in an amount of 0.3 to 10% by weight of the organic solvent, and is particularly preferably dissolved in tetrafluoropropanol in an amount of 0.3 to 10% by weight of the tetrafluoropropanol.

2. The melting point of the dye is 200° C. or higher, and more preferably 300° C. or higher.

3. The molecular weight of the dye is preferably from 300 to 2000.

4. The pyrolysis temperature of the dye is preferably from 200 to 550° C., and more preferably from 250 to 500° C. At this time, the weight reduction thereof is preferably 30% or more, and more preferably 50% or more.

Preferable specific examples of the recording dye are shown below. In the invention, however, the dye is not limited to these examples.

Examples of Compound (Recording Dye) Represented by Formula (I):

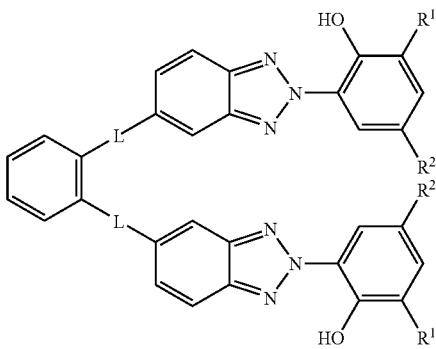

| Compound | L | $R^1$ | $R^2$ |
|---|---|---|---|
| 1 | —NHCO— | Bu(t) | CH$_3$ |
| 2 | —NHCO— | Bu(t) | Bu(t) |
| 3 | —CONH— | Bu(t) | CH$_3$ |
| 4 | —COO— | Bu(t) | Bu(t) |
| 5 | —NCO—<br>\|<br>CH$_3$ | Bu(t) | CH$_3$ |
| 6 | —NCO—<br>\|<br>CH$_3$ | H | CH$_3$ |
| 7 | —CON—<br>\|<br>C$_2$H$_5$ | CH$_3$ | OCH$_3$ |
| 8 | —NHSO$_2$— | CH$_3$ | CH$_3$ |
| 9 | —NHCONH— | Bu(t) | CH$_3$ |
| 10 | —OCO— | Bu(t) | Bu(t) |
| 11 | —S— | CH$_3$ | CH$_3$ |
| 12 | —O— | CH$_3$ | CH$_3$ |
| 13 | —SO$_2$— | Bu(t) | CH$_3$ |
| 14 | —N—<br>\|<br>CH$_3$ | Bu(t) | Bu(t) |
| 15 | —CH$_2$CH$_2$— | CH$_3$ | CH$_3$ |

Compound 16
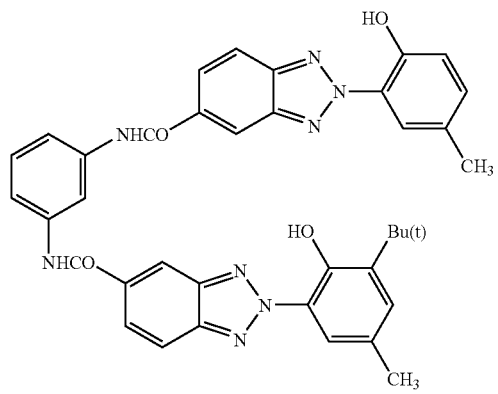
Compound 17
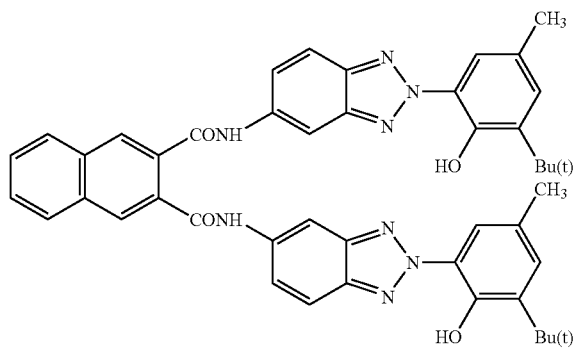
Compound 18
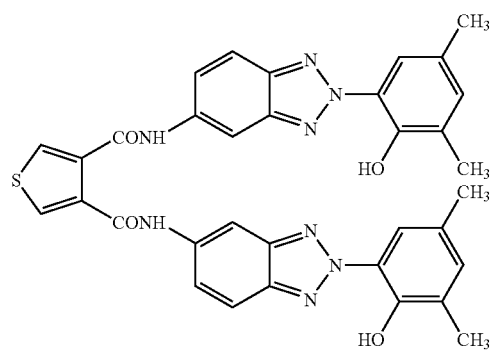
Compound 19
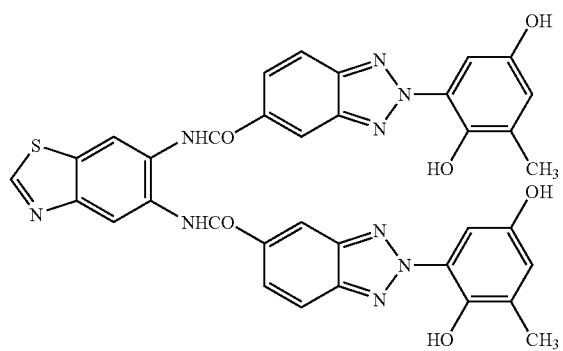
Compound 20
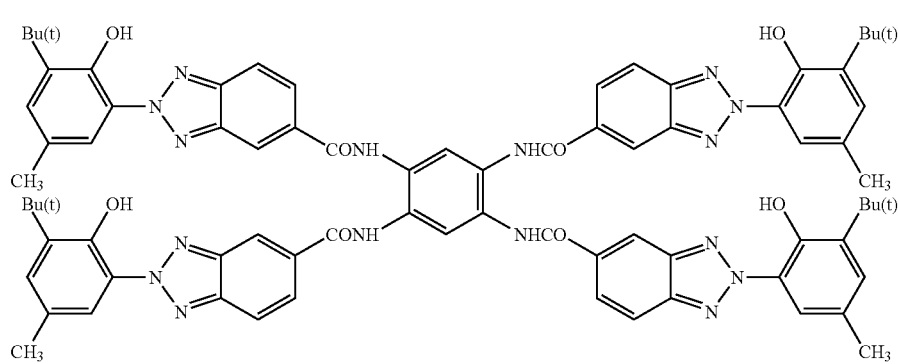

Examples of Compound (Recording Dye) Represented by Formula (III):
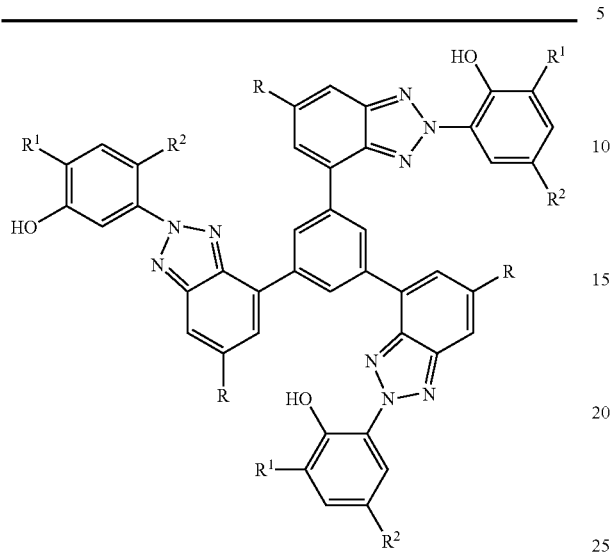
| Compound | R | R¹ | R² |
|---|---|---|---|
| 21 | CH₃ | Bu(t) | CH₃ |
| 22 | CF₃ | Bu(t) | CH₃ |
| 23 | CN | Bu(t) | CH₃ |
| 24 | CO₂CH₃ | Bu(t) | CH₃ |
| 25 | COPh | CH₃ | CH₃ |
| 26 | COCH₃ | CH₃ | CH₃ |
| 27 | SPh | Bu(t) | CH₃ |
| 28 | SO₂Ph | Bu(t) | Bu(t) |
| 29 | OCH₃ | CH₃ | OCH₃ |
| 30 | N(CH₃)₂ | H | CH₃ |
Compound 31
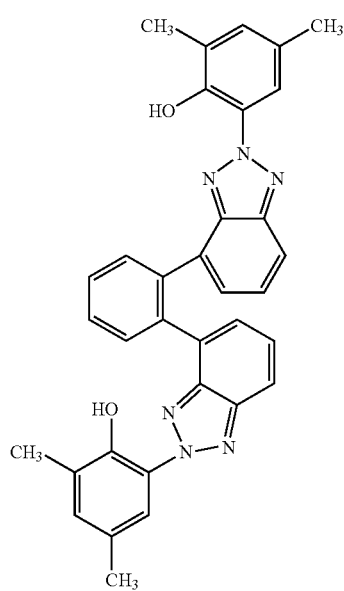
-continued
Compound 32
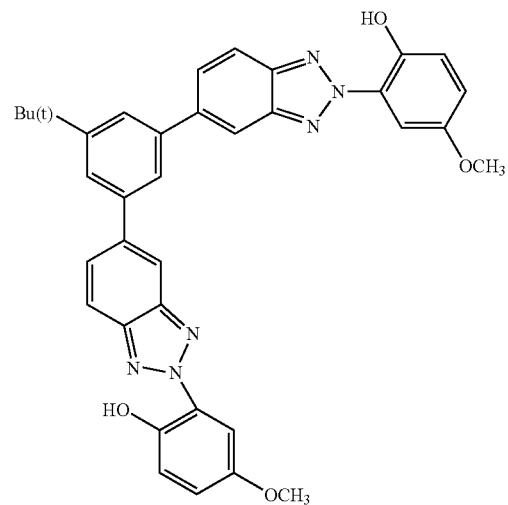
Compound 33
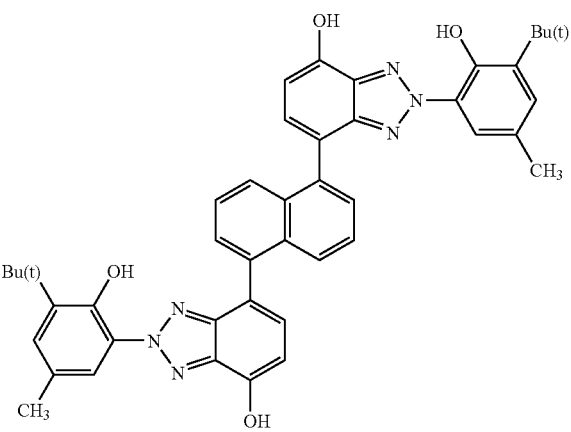
Compound 34
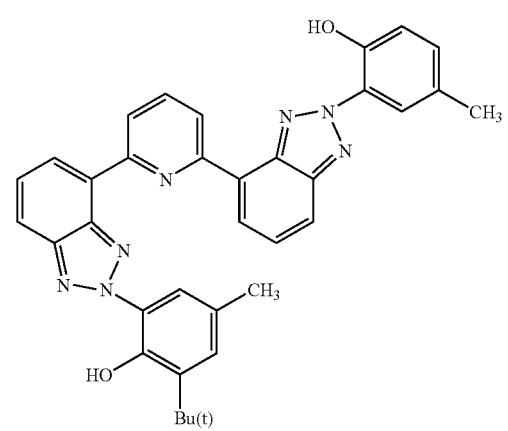

Examples of Compound (Recording Dye) Represented by Formula (II) or (IV):

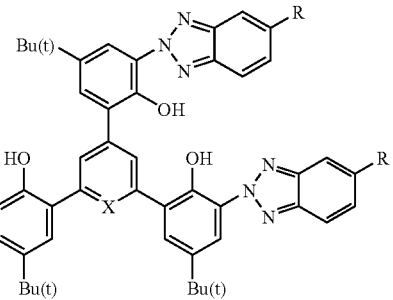

| Compound | R | X |
|---|---|---|
| 35 | CO$_2$CH$_2$CH$_3$ | CH |
| 36 | COPh | CH |
| 37 | SPh | CH |
| 38 | CN | CH |
| 39 | Cl | N |
| 40 | CF$_3$ | CH |

The optical information recording medium of the invention has, on a substrate, a recording layer including a recording dye represented by formula (I) or (II). The optical information recording medium of the invention may have various structures, and preferably has a structure in which the recording layer, a light-reflective layer and a protective layer are disposed in that order on a disc-shaped substrate having a pre-groove at a constant track pitch, or a structure in which a light-reflective layer, the recording layer, and a protective layer are disposed in that order on the disc-shaped substrate. Moreover, another preferable structure of the optical information recording medium is a structure in which two laminates each having the recording layer and a light-reflective layer on a disc-shaped transparent substrate having a pre-groove at a constant track pitch are jointed to each other so that the two recording layers are disposed inward.

In order to attain a higher recording density, a substrate on which a pre-groove having a narrower track pitch than that of a pre-groove of CD-Rs or DVD-Rs is made can be used in the optical information recording medium of the invention. In the optical information recording medium of the invention, the track pitch is preferably from 0.2 to 0.8 µm, more preferably from 0.25 to 0.6 µm, and even more preferably from 0.27 to 0.4 µm.

The depth of the pre-groove is preferably from 0.03 to 0.18 µm, more preferably from 0.05 to 0.15 µm, and even more preferably from 0.06 to 0.1 µm.

A process for producing the optical information recording medium of the invention will be explained hereinafter by way of a medium having, on a disc-shaped substrate, a recording layer, a light-reflective layer and a protective layer in that order.

The substrate of the optical information recording medium of the invention can be made of any material that is used as a material for the substrate of a conventional optical information recording medium. Examples of the material for the substrate include glass, polycarbonate, acrylic resins such as polymethyl methacrylate, vinyl chloride resins such as polyvinyl chloride and polyvinyl chloride copolymers, epoxy resins, amorphous polyolefins, and polyesters. If necessary, these materials may be used in combination. These materials can be used in the form of a film or a rigid substrate. Among the above-mentioned materials, polycarbonate is preferable from the viewpoints of moisture resistance, dimensional stability, and costs.

An undercoat layer may be provided on the substrate surface on which a recording layer is to be formed, in order to improve flatness of the substrate and adhesive strength between the substrate and the recording layer and prevent deterioration of the recording layer. Examples of the material for the undercoat layer include polymer materials such as polymethyl methacrylate, acrylic acid/methacrylic acid copolymers, styrene/maleic anhydride copolymers, polyvinyl alcohol, N-methylolacrylamide, styrene/vinyltoluene copolymers, chlorosulfonated polyethylene, nitrocellulose, polyvinyl chloride, chlorinated polyolefins, polyesters, polyimides, vinyl acetate/vinyl chloride copolymers, ethylene/vinyl acetate copolymers, polyethylene, polypropylene, and polycarbonate; and surface-modifiers such as silane coupling agents. The undercoat layer can be formed by dissolving or dispersing the above-mentioned material in a suitable solvent to prepare a coating solution, and then applying this coating solution onto the surface of the substrate by a coating method such as a spin coating method, a dip coating method, or an extrusion coating method. The thickness of the undercoat layer is generally from 0.005 to 20 µm, and preferably from 0.01 to 10 µm.

The recording layer can be formed by dissolving the above-mentioned recording dye, and, if necessary, a quencher, and a binder in a solvent to prepare a coating solution, applying this coating solution onto the surface of the substrate to form a coating film, and then drying the coating film.

Examples of the solvent in the coating solution include esters such as butyl acetate, ethyl lactate, and cellosolve acetate; ketones such as methyl ethyl ketone, cyclohexanone, and methyl isobutyl ketone; chlorinated hydrocarbons such as dichloromethane, 1,2-dichloroethane, and chloroform; amides such as dimethylformamide; hydrocarbons such as methylcyclohexane; ethers such as dibutyl ether, diethyl ether, tetrahydrofuran, and dioxane; alcohols such as ethanol, n-propanol, isopropanol, n-butanol, and diacetone alcohol; fluorine-containing solvents such as 2,2,3,3-tetrafluoropropanol; and glycol ethers such as ethylene glycol monomethyl ether, ethylene glycol monoethyl ether, and propylene glycol monomethyl ether. These solvents can be used alone or in combination in consideration of solubility of the dye used. Furthermore, the coating solution may contain various additives such as an antioxidant, a UV absorbent, a plasticizer and a lubricant, if necessary.

When the binder is used, examples thereof include natural organic polymer materials such as gelatin, cellulose derivatives, dextran, rosin, and rubber; and synthetic organic polymers such as hydrocarbon resins including polyethylene, polypropylene, polystyrene, and polyisobutylene, vinyl resins including polyvinyl chloride, polyvinylidene chloride, and vinyl chloride/vinyl acetate copolymers, acrylic resins including polymethyl acrylate, and polymethyl methacrylate, polyvinyl alcohol, chlorinated polyethylene, epoxy resin, butyral resin, rubber derivatives, and initially-condensed products of thermoplastic resins including phenol/formaldehyde resins. When the binder is used as one of the materials of the recording layer, the amount (mass) of the binder used is generally from 0.01 to 50 times, and preferably from 0.1 to 5 times as many as the mass of the recording dye. The concentration of the recording dye in the coating solution is generally from 0.01 to 10% by mass, and preferably from 0.1 to 5% by mass.

Examples of the coating method of the coating solution include spray, spin coating, dipping, roll coating, blade coating, and doctor roll methods, and a screen printing method. The recording layer may be monolayered or multilayered. The thickness of the recording layer is generally from 20 to 500 nm, preferably from 30 to 300 nm, and more preferably from 50 to 100 nm.

The recording layer may contain any anti-color fading agent in order to improve light fastness of the recording layer. As the anti-color fading agent, a singlet oxygen quencher is generally used. As the singlet oxygen quencher, those described in known publications such as patent specifications can be used.

Specific examples thereof include singlet oxygen quenchers described in JP-A Nos. 58-175693, 59-81194, 60-18387, 60-19586, 60-19587, 60-35054, 60-36190, 60-36191, 60-44554, 60-44555, 60-44389, 60-44390, 60-54892, 60-47069, 63-209995, and 4-25492, and Japanese Patent Application Publication (JP-B) Nos. 1-38680 and 6-26028, German Patent No. 350399, and the Journal of the Chemical Society of Japan, 1992, October, p. 1141. A preferable example of the singlet oxygen quencher is a compound represented by the following formula (VII):

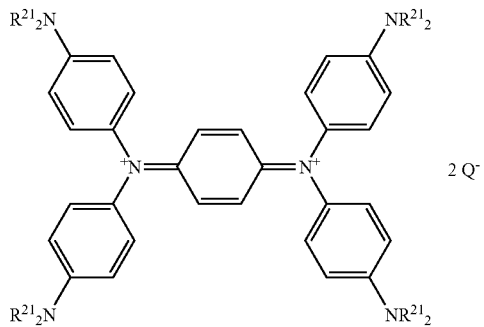

Formula (VII)

wherein $R^{21}$ represents an alkyl group which may have a substituent, and $Q^-$ represents an anion.

In formula (VII), $R^{21}$ is generally an alkyl group which may have a substituent and has 1 to 8 carbon atoms, and is preferably an unsubstituted alkyl group having 1 to 6 carbon atoms. Examples of the substituent of the substituted alkyl group include halogen atoms (such as F or Cl), alkoxy groups (such as methoxy and ethoxy groups), alkylthio groups (such as methylthio and ethylthio groups), acyl groups (such as acetyl and propionyl groups), acyloxy groups (such as acetoxy and propionyloxy groups), a hydroxy group, alkoxycarbonyl groups (such as methoxycarbonyl and ethoxycarbonyl groups), alkenyl groups (such as a vinyl group), and aryl groups (such as phenyl and naphthyl groups). Among these substituents, halogen atoms, alkoxy groups, alkylthio groups and alkoxycarbonyl groups are preferable. Preferable examples of the anion of $Q^-$ include $ClO_4^-$, $AsF_6^-$, $BF_4^-$ and $SbF_6^-$.

Examples of the compound represented by formula (VII) are shown in the following Table 1.

TABLE 1

| Compound No. | $R^{21}$ | $Q^-$ |
|---|---|---|
| VII-1 | $CH_3$ | $ClO_4^-$ |
| VII-2 | $C_2H_5$ | $ClO_4^-$ |
| VII-3 | $n-C_3H_7$ | $ClO_4^-$ |
| VII-4 | $n-C_4H_9$ | $ClO_4^-$ |
| VII-5 | $n-C_5H_{11}$ | $ClO_4^-$ |
| VII-6 | $n-C_4H_9$ | $SbF_6^-$ |
| VII-7 | $n-C_4H_9$ | $BF_4^-$ |
| VII-8 | $n-C_4H_9$ | $AsF_6^-$ |

The use amount of the anti-color fading agent such as the singlet oxygen quencher is usually from 0.1 to 50% by mass, preferably from 0.5 to 45% by mass, more preferably from 3 to 40% by mass, and even more preferably from 5 to 25% by mass of the recording dye.

It is preferred to form a light-reflective layer adjacently to the recording layer in order to improve reflectivity of the recording medium at the time of reproducing information. The material of the light-reflective layer is a light-reflective material, which is a material having a high reflectivity to laser beams. Examples thereof include metals and semimetals, such as Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn and Bi; and stainless steel. These materials may be used alone, or in combination, or may be used in the form of alloy. Among these examples, preferable are Cr, Ni, Pt, Cu, Ag, Au, Al and stainless steel. Particularly preferable are Au, Ag and Al metals, and alloys thereof. The most preferable are Ag and Al metals, and alloys thereof. The light-reflective layer can be formed on the substrate or the recording layer, for example, by vapor-depositing, sputtering or ion-plating the light-reflective material. The thickness of the light-reflective layer is generally from 10 to 300 nm, and preferably from 50 to 200 nm.

It is preferable to form, on the light-reflective layer or the recording layer, a protective layer in order to physically and chemically protect the recording layer or the like. When the optical information recording medium has the same structure as that of DVD-R type optical information recording media, that is, when the medium has a structure in which two substrates are bonded to each other so that their recording layers are disposed inward, it is unnecessary to form the protective layer. Examples of the material used in the protective layer include inorganic materials such as SiO, $SiO_2$, $MgF_2$, $SnO_2$, and $Si_3N_4$; and organic materials such as thermoplastic resins, thermosetting resins and UV curable resins. The protective layer can be formed, for example, by laminating on the reflective layer a film (transparent sheet) obtained by extruding a plastic with an adhesive agent, or by vacuum-evaporating, sputtering, or applying the protective layer material. When the protective layer is made of the thermoplastic resin or the thermosetting resin, the protective layer can be formed by dissolving the resin in a suitable solvent to prepare a coating solution, applying this coating solution to the recording layer or the light-reflective layer, and then drying the applied layer. When the protective layer is made of the UV curable resin, the protective layer can be formed by applying the resin as it is or applying a coating solution prepared by dissolving the resin in a suitable solvent, and then radiating UV light onto the applied layer so as to cure the resin. The coating solution may contain various additives such as an antistatic agent, an antioxidant, and a UV absorbent, if necessary. In general, the thickness of the protective layer (or the thickness of the transparent sheet if the sheet is used as the protective layer) is preferably from 0.1 μm to 1 mm.

Since the optical information recording medium of the invention includes the above-mentioned recording dye in the recording layer thereof, the medium has a high refractive index to light having a wavelength of 440 nm or less. Dependently on the recording dye used, the absorption coefficient of the medium can be high or low in a suitable wavelength range. As a result, the optical information recording medium can exhibit a high sensitivity to short wavelength laser beams having a wavelength of 440 nm or less, and can have a high reflectivity and a high degree of modulation thereto. Since the above-mentioned recording dye has high fastness, the recording medium is excellent in terms of moisture and heat resistance and light stability and further the recording layer made of the dye is satisfactory in terms of strength and film quality.

2. Dye Compound

The dye compound of the invention is represented by the following formula (V) or the following formula (VI):

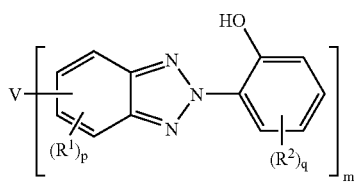

Formula (V)

wherein $R^1$ and $R^2$ each independently represent a substituent, p and q are each an integer of 0 to 3, m is an integer of 2 or 3, and V represents an aromatic ring, which may have a substituent,

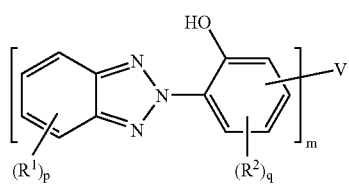

Formula (VI)

wherein $R^1$, $R^2$, p, q, V and m represent the same definitions as those of $R^1$, $R^2$, p, q, V and m in formula (V), respectively.

In the dye compound of the invention, examples of $R^1$, $R^2$, p, q, V and m are the same as those described in the explanations for the above-mentioned recording dye. Examples of the dye compound are also the same as those described in the explanations for the recording dye.

The dye compound can be applied to any optical information recording medium including a dye recording layer since the dye compound is superior in fastness. Since the dye compound has a high refractive index to light having a wavelength of 440 nm or less, it is preferred to apply the dye compound to the recording dye of the optical information recording medium of the invention.

The method for producing the dye compound of the invention will be described in Synthesis Examples described later.

3. Information Recording Method

In the information recording method of the invention, information is recorded onto an optical information recording medium having, on a substrate, a recording layer on which the information can be recorded by radiating thereto laser beams having a wavelength of 440 nm or less and which includes the above-mentioned recording dye.

Specifically, the method can be performed by using the optical information recording medium of the invention as follows.

While the optical information recording medium is rotated at a constant linear velocity or a constant angular velocity, recording light such as semiconductor laser beams is first radiated onto the medium from the substrate side or the protective layer side. Then, the recording layer absorbs the light, so that the temperature of the recording layer rises locally. As a result, a physical or chemical property of the irradiated portions of the recording layer changes (for example, pits are generated), so that the optical property of the recording layer locally changes. Thus, information is recorded on the medium. In the invention, as a source of the recording light, a semiconductor laser having an oscillation wavelength ranging from 390 to 450 nm may be used. Preferable examples of the light source include bluish purple light-emitting semiconductor lasers having an oscillation wavelength ranging from 390 to 415 nm, and bluish purple light-emitting SHG lasers having a central oscillation wavelength of 425 nm, in which SHG lasers an optical waveguide element is used to reduce the central oscillation wavelength (850 nm) of infrared semiconductor lasers to half. Among these, the bluish purple light-emitting semiconductor lasers are particularly preferable since a high recording density can be attained. The information recorded as described above can be reproduced by radiating semiconductor laser beams onto the optical information recording medium from the substrate side or the protective layer side while the medium is rotated at the same linear velocity as that described above, and detecting light reflected by the medium.

EXAMPLES

The present invention will be described in more detail by way of the following examples. However, the invention is not limited to the examples.

Synthesis Example 1

Synthesis of Compound 1 Exemplified as Recording Dye 0.33 g of 5-carboxy-2-(2-hydroxy-3-tert-butyl-5-methylphenyl)-2H-benzotriazole was dissolved in 20 ml of methylene chloride. 0.1 ml of oxazolyl chloride was added to the resultant solution. The resulting solution was stirred at room temperature for 1 hour, and then 54 mg of phenylenediamine and 0.3 ml of triethylamine were added to the solution. The resultant solution was stirred for 2 hours, and then water was added to the solution, so as to extract the organic material with methylene chloride. This methylene chloride solution was dried with sodium sulfate and then the solvent of the solution was distilled off. The remaining solid was washed with ethyl acetate and 0.3 g of compound 1 was obtained.

λmax=361 nm ($CHCl_3$) Mass (posi)=722

Synthesis Example 2

Synthesis of Compound 21 Exemplified as Recording Dye

Five milliliter of an aqueous solution in which 0.5 g of sodium carbonate was dissolved in 5 ml of toluene was added to 0.5 g of 4-bromo-6-methyl-2-(2-hydroxy-3-tert-butyl-5-methylphenyl)-2H-benzotriazol, 0.18 g of pinacol ester of benzene-1,3,5-triboric acid, and 15 mg of palladium acetate. 27 mg of tri-tert-butylphosphine was added to the resultant solution while the solution was stirred under nitrogen flow. The resultant solution was stirred at 80° C. for 10 hours, and then 1 N hydrochloric acid was added thereto. After the resultant mixture separated into two phases, the aqueous phase was removed. The remaining organic phase was dried with sodium sulfate and the solvent in the organic phase was distilled off. The remaining solid was purified with silica gel chromatography and 0.3 g of compound 21 was obtained.

λmax=349 nm (CHCl$_3$) Mass (posi)=958

Synthesis Example 3

Synthesis of Compound 40 Exemplified as Recording Dye

Five milliliter of an aqueous solution in which 0.5 g of sodium carbonate was dissolved in 5 ml of toluene was added to 0.6 g of pinacol ester of 5-tert-butyl-3-(5-trifluoromethyl-2H-benzotriazolyl)-2-hydroxyphenylboric acid, 0.18 g of 1,3,5-triiodobenzene and 15 mg of palladium acetate. 27 mg of tri-tert-butylphosphine was added to the resultant solution while the solution was stirred under nitrogen flow. The resultant solution was stirred at 80° C. for 10 hours, and then 1 N hydrochloric acid was added thereto. After the resultant mixture separated into two phases, the aqueous phase was removed. The remaining organic phase was dried with sodium sulfate and the solvent in the organic phase was distilled off. The remaining solid was purified with silica gel chromatography and 0.2 g of compound 40 was obtained.

λmax=359 nm (CHCl$_3$) Mass (posi)=1078

Synthesis Examples of the above-mentioned recording dyes (dye compounds) are mere examples, and the recording dyes applied to the invention (i.e., the recording dyes represented by formulae (I) to (IV)) can be prepared by modifying the Synthesis Examples in various ways.

Example 1

Compound 1 exemplified as the recording dye was dissolved in methylcyclohexane to yield a recording layer coating solution (concentration: 1% by mass). A polycarbonate substrate (diameter: 120 mm, thickness: 0.6 mm) on the surface of which a spiral pre-groove (track pitch: 0.4 μm, groove width: 0.2 μm, and groove depth: 0.08 μm) was formed by injection molding was prepared. The coating solution was applied onto the pre-groove-formed surface of the substrate by spin coating so as to form a recording layer (thickness thereof in the pre-groove: about 80 nm).

Next, silver was sputtered onto the recording layer to form a light-reflective layer having a thickness of about 100 nm.

Furthermore, a UV curable resin (SD 318 manufactured by Dainippon & Ink Chemicals, Inc.) was applied onto the light-reflective layer. Then, the applied resin was exposed to ultraviolet rays so as to cure the resin, thereby forming a protective layer having a thickness of 7 μm.

An optical information recording medium of the invention was thus obtained.

Examples 2 to 8

Optical information recording media of the invention were produced in the same way as in Example 1 except that compound 1 was changed to compounds shown in Table 2 (without changing the amount thereof).

Comparative Examples 1 to 5

Optical information recording media for comparison were produced in the same way as in Example 1 except that compound 1 was changed to comparative dye compounds A to E (without changing the amount thereof) and the solvent of the coating solution was changed to 2,2,3,3-tetrafluoropropanol.

The comparative dye compounds A to E are shown bellow.

Comparative Compounds (A) Compound Described in Example 1 of JP-A No. 4-74690

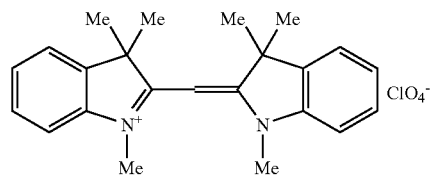

(B) Compound (III) Described in Example 1 of JP-A No. 11-334205

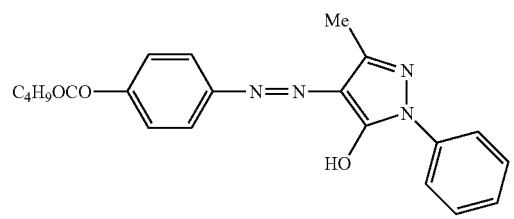

(C) Specific Example (14) Described in JP-A No. 2002-172865

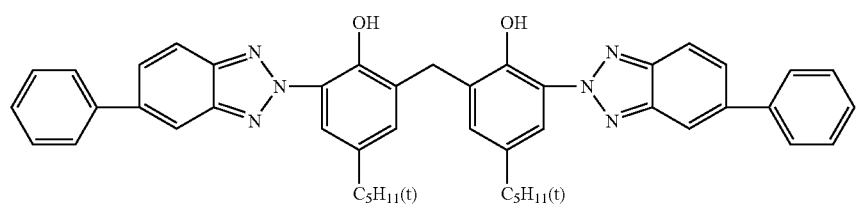

(D) Specific Example (15) Described in Examples of JP-A No. 2002-172865

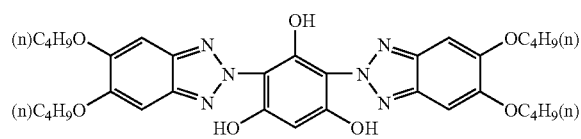

(E) Specific Example (18) Described in JP-A No. 2002-163799

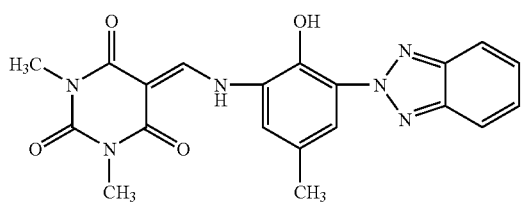

Evaluation of Optical Information Recording Media

A semiconductor laser having an oscillation wavelength of 405 nm and emitting bluish purple light was used to record 14T-EFM signals onto each of the produced optical information recording media at a linear velocity of 3.5 m/second. Thereafter, the recorded signals were reproduced. The degree of modulation of each medium, reflectivity of the non-recorded portions of each medium, and sensitivity of each medium were measured at an optimal power. Light from a xenon light source having an illuminance of 100,000 lux was radiated onto each of the optical discs for 3 days without using any UV filter. Thereafter, reflectivity of the non-recorded portions of each medium was measured. A DDU 1000 (trade name) manufactured by Pulstec Industrial Co., Ltd. was used to perform recording and evaluation of recording properties of the media. The evaluation results are shown in the following Table 2.

It can be understood from the results shown in Table 2 that the optical discs of the invention (Examples 1 to 8) exhibits a higher reflectivity to the bluish purple semiconductor laser beams and have a higher degree of modulation and a higher sensitivity thereto than the optical discs having the recording layers which contained the comparative compounds A to E, respectively.

Accordingly, it has been understood that optical discs having high recording properties to short wavelength laser beams can be obtained by using the recording dyes of the invention. It has also been confirmed that recording layers made of the recording dye have sufficient strength and high light fastness.

What is claimed is:
1. An optical information recording medium comprising:
   a disc-shaped substrate, a surface of which has a pre-groove having a track pitch of 0.2 to 0.8 μm; and
   a recording layer comprising a recording dye represented by either of the following formulae (V) or (VI) on the surface of the substrate having the pre-groove:

Formula (V)

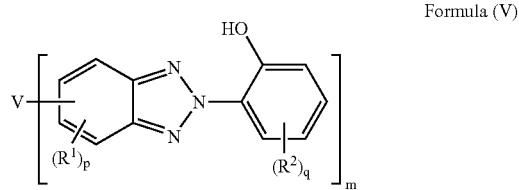

wherein $R^1$ and $R^2$ each independently represent a substituent, p and q are each an integer of 0 to 3, m represents a number of valence bonds between 2 to 4, and when m=2 V is selected from the group consisting of a 2,3-naphthylene group, a 1,5-naphthylene group, a 3,4-thiophenylene group, a 5,6-benzthiazolylene group, and a 2,6-pyridinylene group each of which may have a substituent; when m=3 V is selected from the group consisting of a benzene-1,3,5-triyl group and a 2,4,6-pyridinylene group each of which may have a

TABLE 2

| | Dye compound in recording layer | Reflectivity (%) of non-recorded portions | Modulation degree (%) | Sensitivity (mW) | Reflectivity (%) of non-recorded portions (after light radiation) |
|---|---|---|---|---|---|
| Example 1 | (1) | 72 | 62 | 6.1 | 72 |
| Example 2 | (6) | 69 | 58 | 6.2 | 69 |
| Example 3 | (18) | 68 | 63 | 7.2 | 68 |
| Example 4 | (20) | 74 | 64 | 6.4 | 74 |
| Example 5 | (21) | 70 | 68 | 6.7 | 70 |
| Example 6 | (23) | 70 | 68 | 5.2 | 70 |
| Example 7 | (35) | 71 | 65 | 6.3 | 71 |
| Example 8 | (37) | 63 | 66 | 5.6 | 62 |
| Comparative Example 1 | (A) | 35 | 58 | 7.9 | 0 |
| Comparative Example 2 | (B) | 36 | 41 | 9.7 | 0 |
| Comparative Example 3 | (C) | 66 | 58 | 7.3 | 0 |
| Comparative Example 4 | (D) | 73 | 65 | 6.5 | 55 |
| Comparative Example 5 | (E) | No signals were able to be recorded since the recording layer whitened. | | | | substituent; and when m=4 V is a benzene-1,2,4,5-tetrayl group which may have a substituent, Formula (VI)

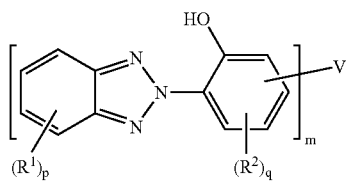

wherein $R^1$, $R^2$, p, q, V and m represent the same definitions as those of $R^1$, $R^2$, p, q, V and m in formula (V), respectively.

2. The optical information recording medium of claim 1, wherein in both formulae (V) and (VI), V represents a benzene-1,3,5-triyl group, a benzene-1,2,4,5-tetrayl group or a 2,4,6-pyridinylene group, which may have a substituent, respectively.

3. The optical information recording medium of claim 1, wherein in both formulae (V) and (VI), m represents an integer of 3 and V represents a benzene-1,3,5-triyl group or a 2,4,6-pyridinylene group, which may have a substituent, respectively.

4. The optical information recording medium of claim 1, further comprising a light-reflective layer made of a metal, between the recording layer and the surface of the substrate having the pre-groove.

5. The optical information recording medium of claim 4, further comprising a protective layer on the recording layer.

6. A method for recording information onto an optical information recording medium, the optical information recording medium comprising:
a disc-shaped substrate, a surface of which has a pre-groove having a track pitch of 0.2 to 0.8 μm; and
a recording layer comprising a recording dye represented by either of the following formulae (V) or (VI) on the surface of the substrate having the pre-groove:

Formula (V)

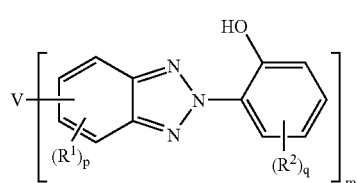

wherein $R^1$ and $R^2$ each independently represent a substituent, p and q are each an integer of 0 to 3, m represents a number of valence bonds between 2 to 4, and when m=2 V is selected from the group consisting of a 2,3-naphthylene group, a 1,5-naphthylene group, a 3,4-thiophenylene group, a 5,6-benzthiazolylene group, and a 2,6-pyridinylene group each of which may have a substituent; when m=3 V is selected from the group consisting of a benzene-1,3,5-triyl group and a 2,4,6-pyridinylene group each of which may have a substituent; and when m=4 V is a benzene-1,2,4,5-tetrayl group which may have a substituent, Formula (VI)

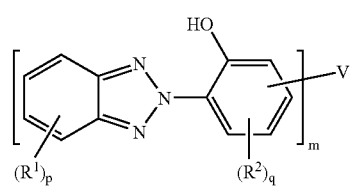

wherein $R^1$, $R^2$, p, q, V and m represent the same definitions as those of $R^1$, $R^2$, p, q, V and m in formula (V), respectively, the method comprising:

providing a laser that emits light having a wavelength equal to or less than 440 nm, and using the laser to record information on the optical information recording medium.

7. The information recording method of claim 6, wherein the optical information recording medium further comprises a light-reflective layer made of a metal, between the recording layer and the surface of the substrate having the pre-groove.

8. The information recording method of claim 7, wherein the optical information recording medium further comprises a protective layer on the recording layer.

9. The information recording method of claim 8, wherein the laser emits light having a wavelength of 405 nm.

10. A dye compound represented by either of the following formulae (V) or (VI):

wherein $R^1$ and $R^2$ each independently represent a substituent, p and q are each an integer of 0 to 3, m represents a number of valence bonds between 2 to 4, and when m=2 V is selected from the group consisting of a 2,3-naphthylene group, a 1,5-naphthylene group, a 3,4-thiophenylene group, a 5,6-benzthiazolylene group, and a 2,6-pyridinylene group each of which may have a substituent; when m=3 V is selected from the group consisting of a benzene-1,3,5-triyl group and a 2,4,6-pyridinylene group each of which may have a substituent; and when m=4 V is a benzene-1,2,4,5-tetrayl group which may have a substituent, Formula (V)

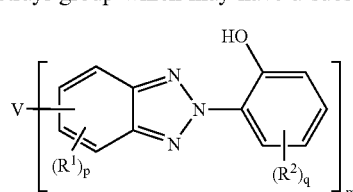

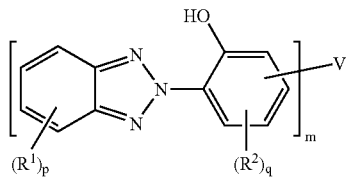

Formula (VI)

wherein R¹, R², p, q, V and m represent the same definitions as those of R¹, R², p, q, V and m in formula (V), respectively.

11. The dye of claim 10, wherein in both formulae (V) and (VI), m represents a number of valence-bond and V represents an aromatic ring selected from the group consisting of a benzene-1,3,5-triyl group, a benzene-1,2,4,5-tetrayl group, and a 2,4,6-pyridinylene group, which may have a substituent.

12. The dye of claim 10, wherein in both formulae (V) and (VI), m represents an integer of 3 and V represents an aromatic ring selected from the group consisting of a benzene-1,3,5-triyl group and a 2,4,6-pyridinylene group, which may have a substituent.

13. The dye of claim 12, wherein the dye is selected from the group consisting of the following Compounds 21 to 30 and 35 to 40:

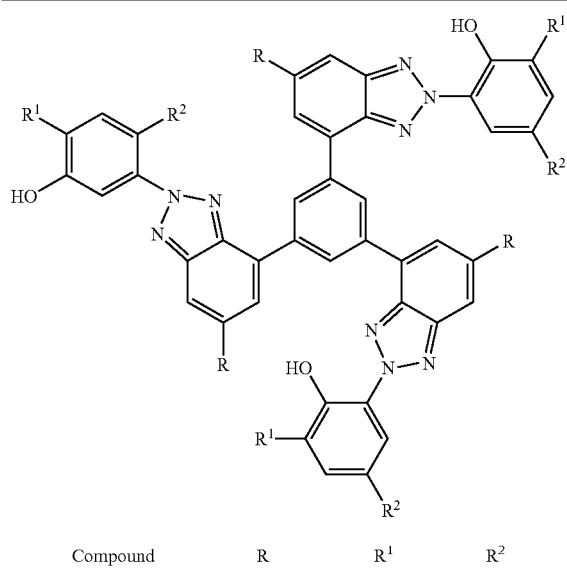

| Compound | R | R¹ | R² |
|---|---|---|---|
| 21 | CH₃ | Bu(t) | CH₃ |
| 22 | CF₃ | Bu(t) | CH₃ |
| 23 | CN | Bu(t) | CH₃ |
| 24 | CO₂CH₃ | Bu(t) | CH₃ |
| 25 | COPh | CH₃ | CH₃ |
| 26 | COCH₃ | CH₃ | CH₃ |

-continued

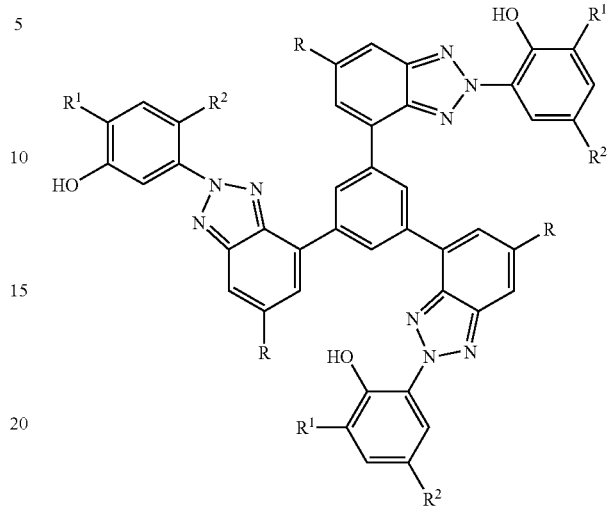

| Compound | R | R¹ | R² |
|---|---|---|---|
| 27 | SPh | Bu(t) | CH₃ |
| 28 | SO₂Ph | Bu(t) | Bu(t) |
| 29 | OCH₃ | CH₃ | OCH₃ |
| 30 | N(CH₃)₂ | H | CH₃ |

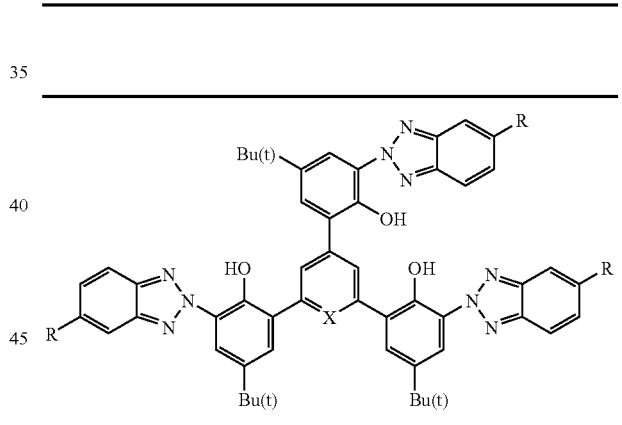

| Compound | R | X |
|---|---|---|
| 35 | CO₂CH₂CH₃ | CH |
| 36 | COPh | CH |
| 37 | SPh | CH |
| 39 | Cl | N |
| 40 | CF₃ | CH. |

* * * * *